United States Patent [19]

Nakamura et al.

[11] Patent Number: 4,704,473
[45] Date of Patent: Nov. 3, 1987

[54] 4-METHOXY-2'-CARBOXYDIBENZOYLMETHANE AND ITS SALTS

[75] Inventors: Koichi Nakamura, Tochigi; Kimihiko Hori, Utsunomiya; Michihiro Hattori, Utsunomiya; Toru Tejima, Tochigi; Genji Imokawa; Naotake Takaishi, both of Utsunomiya, all of Japan

[73] Assignee: Kao Corporation, Tokyo, Japan

[21] Appl. No.: 804,598

[22] Filed: Dec. 4, 1985

[30] Foreign Application Priority Data

Dec. 11, 1984 [JP] Japan .................. 59-261654

[51] Int. Cl.$^4$ ............................................. C07C 59/90
[52] U.S. Cl. ............................ 562/463; 260/501.1; 260/501.17; 514/568
[58] Field of Search .............. 562/463; 260/501.1, 260/501.17; 514/568

[56] References Cited

U.S. PATENT DOCUMENTS 4,381,360 4/1983 Leistner et al. .................. 562/463

Primary Examiner—Paul J. Killos
Attorney, Agent, or Firm—Oblon, Fisher, Spivak, McClelland & Maier

[57] ABSTRACT

4-methoxy-2'-carboxydibenzoylmethane of the following general formula (I)

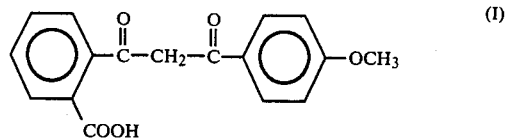

is prepared by reacting p-methoxyacetophenone (III) with phthalic anhydride (II) in accordance with the following reaction equation.

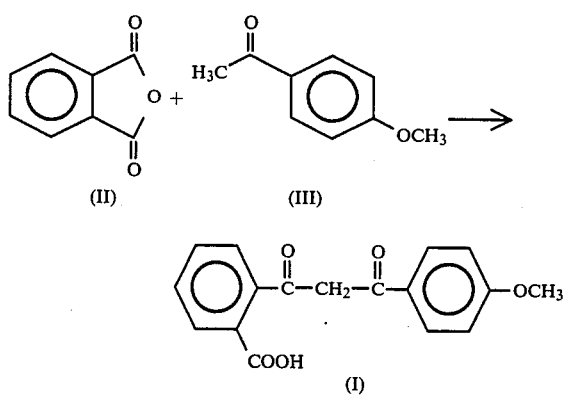

The compound (I) and its salts absorb both UV-A and UV-B, and exhibit prominent effects as a ultraviolet absorber for cosmetic formulations such as skin cosmetic formulations and hair cosmetic formulations.

15 Claims, 1 Drawing Figure

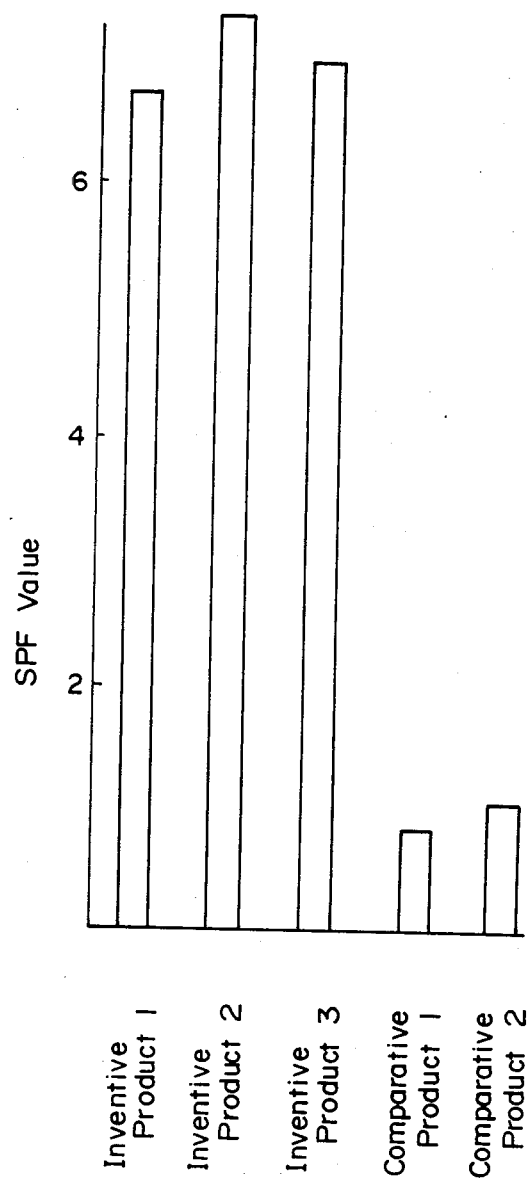
FIGURE

4-METHOXY-2'-CARBOXYDIBENZOYLMETHANE AND ITS SALTS

FIELD OF THE INVENTION

This invention relates to novel 4-methoxy-2'-carboxydibenzoylmethane and its salts, all of which have prominent ultraviolet absorbing effects.

BACKGROUND OF THE INVENTION

Ultraviolet radiation is known to induce various changes in the skin. Dermatologically, active wavelengths are divided into long-wavelength ultraviolet rays of 400-320 nm, medium-wavelength ultraviolet rays of 320-290 nm and short-wavelength ultraviolet rays shorter than 290 nm, which are called "UV-A", "UV-B" and "UV-C" respectively.

The majority of ultraviolet radiation sources to which human are exposed is usually sun light. Ultraviolet radiation which reaches the ground are UV-A and UV-B, while UV-C is absorbed in the ozonosphere and practically does not reach the ground. Of ultraviolet radiation which reaches the ground, UV-B induces changes in the skin, for example, development of erythema and blisters, enhancement of the formation of melanin, and cause of pigmentation when irradiated to the skin beyond a certain energy level. On the other hand, UV-A has conventionally been considered not to give too much changes to the skin. In recent years, it has however been found by electron microscopes or some histochemical methods that the skin may be affected upon its exposure to UV-A. Especially, unlike UV-B, the energy of UV-A reaches as deep as the corium, whereby the elastic fibers in vessel walls and connective tissue are caused to undergo semi-chronic changes. These changes are believed to lead to the acceleration of skin aging. UV-A is also known to make the skin darker immediately after its irradiation (immediate pigmentation) and to enhance the deleterious effects of UV-B to the skin. Accordingly, UV-A is considered to serve as one of causes for the occurrence or aggravation of chloasma or freckles.

As readily understood from the foregoing, it is important to protect the skin not only from UV-B but also from UV-A for the prevention of accelerated aging of the skin and the avoidance of occurrence or aggravation of chloasma or freckles.

It is however not very long since researches started on the effects of UV-A to the skin. Under the circumstances, there are not known many materials which can effectively absorb UV-A when applied to the skin. For the time being, dibenzoylmethane derivatives and cinnamic acid derivatives are only known to have such effects. Most of them are however fat-soluble (see, DE-OS No. 27 28 241 and 27 28 243; and Japanese Patent Laid-Open Nos. 61641/1976, 46056/1977 and 197209/1982), and there are only handful water-soluble materials (see, Japanese Patent Laid-Open No. 59840/1982). If one wants to incorporate such UV-A absorbents to cosmetic formulations, various limitations are imposed on the properties of the base materials in such cosmetic formulations. There is thus an outstanding demand for the development of a UV-A absorbent which has broader applicability. Such a UV-A absorbent is supposed to satisfy the following conditions.

(1) To have the maximum absorption wavelength around a wavelength of 350 nm.

(2) To have sufficiently large molar extinction coefficient ($\epsilon$) at the above wavelength.

(3) To absorb little visible light, namely, to have $\epsilon \approx 0$ at wavelengths of 400 nm and longer because it is not desirable to color cosmetic formulations.

(4) To be stable to heat and light.

(5) To have no toxicity, irritation and any other harmful effects to the skin.

(6) To have excellent compatibility with the base materials of cosmetics.

(7) To be resistant to percutaneous absorption and less susceptible to removal due to perspiration when applied to the skin, in other words, to maintain its effects effectively for a long period of time.

(8) To be inexpensive.

SUMMARY OF THE INVENTION

With the foregoing in view, the present inventors have carried out an extensive research and as a result, have found that 4-methoxy-2'-carboxydibenzoylmethane of the following general formula (I):

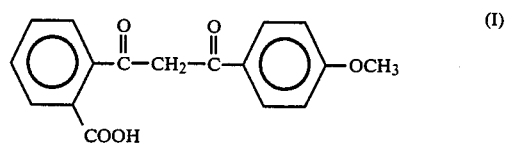

and its salts absorb both UV-A and UV-B and exhibit prominent effects as an ultraviolet absorbent for cosmetic formulations such as skin cosmetic formulations and hair cosmetic formulations. The present invention has been accomplished based on the above finding.

Accordingly, an object of the present invention is to provide novel 4-methoxy-2'-carboxydibenzoylmethane of the formula (I) and its salts.

Incidentally, U.S. Pat. No. 4,381,360 discloses certain dibenzoylmethane derivatives the generic concept of which embraces the compound (I) of this invention. However, it discloses only their stabilizing effects for polyvinyl halide resins and is absolutely silent above ultraviolet absorbing effects of such compounds. In addition, the compound (I) of this invention is a novel compound which is not elucidatively disclosed in the above-cited patent specification. Moreover, the compound (I) of this invention has particularly-good ultraviolet absorbing effects compared with the compounds recited by way of example in the patent specification.

BRIEF DESCRIPTION OF THE DRAWINGS

The sole FIGURE is a graph showing the SPF values of Inventive Product Nos. 1-3 and Comparative Product Nos. 1 and 2.

DETAILED DESCRIPTION OF THE INVENTION AND PREFERRED EMBODIMENTS

As exemplary salts of 4-methoxy-2'-carboxydibenzoylmethane, may be mentioned its alkali metal salts such as its lithium, sodium and potassium salts, its basic amino acid salts such as its lysine and arginine salts, its organic amine salts such as its mono-, di- or triethanolamine salt, etc.

No particular limitation is imposed to the preparation process of the compound (I) of this invention. For example, it may be prepared by reacting p-methoxyacetophenone (III) with phthalic anhydride (II) in accordance with the following reaction scheme.

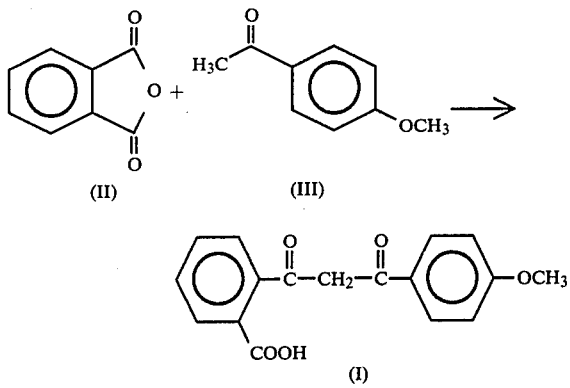

In order to practice the above process, the enolate of p-methoxyacetophenone is prepared first of all. Namely, p-methoxyacetophenone and a base such as sodium hydride, sodium alcoholate or sodium amide are reacted at a temperature of 100° C. or higher in an inert solvent such as toluene or xylene. While taking out of the reaction system hydrogen gas, ammonia gas, alcohols and the like which occur as the reaction proceeds, the reaction mixture is further heated under reflux to complete the reaction. The liquid reaction mixture was then cooled to 20°–100° C., preferably, to 60° C., followed by an addition of phthalic anhydride with vigorous stirring so that the phthalic anhydride is reacted further. The solvent was then distilled-off from the liquid reaction mixture. The resultant slurry was added with a suitable organic solvent and an aqueous solution of an appropriate acid. After washing the resulting organic layer with water until its pH falls within the range of from 5 to 6, the solvent is distilled-off to obtain the intended product (I). It may then be converted to a salt by a method known per se in the art.

4-Methoxy-2'-carboxydibenzoylmethane of this invention is in the form of colorless and odorless crystals and as demonstrated in Tests which will be given herein, absorbs both UV-A and UV-B, and is thus useful as an ultraviolet absorbent for cosmetic formulations.

The present invention will hereinafter be described in the following Examples and Tests. It should however be borne in mind that the present invention is not necessarily limited to or by them.

EXAMPLE 1

(i) Preparation of 4-methoxy-2'-carboxydibenzoylmethane:

Placed in a 1 l flask fitted with a reflux condenser were 700 ml of xylene, which had been azeotropically dried, and 99.2 g (0.51 mole) of sodium methylate (as a 28% solution in methanol). The contents were heated to 110° C. to distill-off the methanol. The resulting solution was added to 30 g (0.2 mole) of p-methoxyacetophenone, and the thus-obtained mixture was heated again to 110° C. while distilling-off methanol which was being formed. After completion of discharge of methanol by its distillation, the reaction mixture was heated further at the refluxing temperature of the solvent so as to bring the reaction to completion. The resultant reaction mixture was then cooled to 60° C., followed by an addition of 35 g (0.24 mole) of phthalic anhydride while vigorously stirring the reaction mixture. The reaction proceeded exothermically. As the reaction proceeded, more and more salt precipitated and the liquid reaction solution was converted into a slurry. After completion of the reaction, the xylene was distilled-off and the resultant slurry was added to 700 ml of methyl ethyl ketone and 160 g of a 12% aqueous solution of hydrochloric acid. By stirring the resultant mixture, the solid matter was dissolved in its entirety. After separating and collecting the organic layer, it was washed three times with 100 ml of deionized water and the solvent was distilled-off under reduced pressure to obtain yellowish solid matter. It was then dissolved in 200 ml of hot ethanol. Upon cooling the ethanol solution to room temperature, 52.1 g of the intended compound, 4-methoxy-2'-carboxybenzoylmethane, was obtained as slightly yellowish crystals. Yield: 87%.

m.p.: 156°–158° C.

IR (KBr cm$^{-1}$): 2950, 1690, 1590, 1500, 1460, 1440, 1415, 1290, 1255, 1225, 1175, 1020, 930, 850, 805, 775.

NMR (CD$_3$OD)δ: 3.85 (s, 3H, —OCH$_3$); 6.90–7.07 (m, 2H, aromatic protons); 7.53–8.04 (m, 6H, aromatic protons).

(ii) Preparation of 4-methoxy-2'-carboxydibenzoylmethane sodium salt:

In a 300 ml Erlenmeyer flask, 1.26 g (30 millimoles) of 95% sodium hydroxide was dissolved at room temperature in a mixed solvent containing 50 ml of deionized water and 100 ml of ethanol. A 9.8 g (33 millimoles) of 4-methoxy-2'-carboxydibenzoylmethane dissolved in 100 ml of ethanol was added to the resultant solution at room temperature. After stirring the resultant mixture at room temperature for 10 minutes, the solvent was distilled-off and the resulting slightly-yellowish amorphous matter was again dissolved in 150 ml of deionized water. The thus-obtained solution was washed three times with 50 ml of chloroform so as to remove any excess 4-methoxy-2'-carboxydibenzoylmethane. After washing, water was distilled-off to obtain slightly-yellowish amorphous matter. It was then recrystallized from a mixed solvent of water and ethanol, thereby obtaining 9.86 g of the intended 4-methoxy-2'-carboxydibenzoylmethane sodium salt as slightly-yellowish crystals. Yield: 94%.

m.p.: 180° C. and up (turned to a reddish brown color due to decomposition)

IR (KBr cm$^{-1}$): 3450, 1600, 1550, 1495, 1440, 1425, 1400, 1305, 1250, 1215, 1175, 1020, 845.

NMR (D$_2$O, δ): 3.72 (s, 3H, —OCH$_3$); 6.78–6.95 (m, 2H, aromatic protons); 7.27–7.57 (m, 4H, aromatic protons); 7.67–7.83 (m, 2H, aromatic protons).

Test 1:

Using creams containing compounds of this invention in an amount of 2%, the effects of the compounds in protecting the skin from the radiation of UV-A were investigated. In this Test, were employed a cream (Inventive Product No. 1) of the composition described in the below-described Example 3, another cream (Inventive Product No. 2) obtained by substituting 4-methoxy-2'-carboxydibenzoylmethane sodium salt for 4-methoxy-2'-carboxydibenzoylmethane in the cream composition of Example 3 and a further cream (Inventive Product No. 3) obtained by substituting 4-methoxy-2'-carboxydibenzoylmethane arginine salt for 4-methoxy-2'-carboxydibenzoylmethane in the cream composition of Example 3. The tests were carried out in accordance with the method proposed by Gschnait et al in "Archives of Dermatological Research", 263, 181–188 (1978). Namely, the dorsal hairs of guinea pigs were shaved to expose their skins. Their sensitivity to UV-A were in advance increased by intraperitoneal administration of 8-methoxyproralen. Thereafter, each cream including the above-described inventive products was applied to the exposed dorsal skins to give coat weights of 2 mg/cm². Fifteen minutes later, UV-A was irradiated. On the next day, the extents of erythema developed on their skins were observed to determine the minimum UV-A irradiation time periods required to develop erythema on the skins. Comparing those time periods with their corresponding minimum time periods of UV-A irradiation required to develop erythema on the respective uncoated skins, the sun protecting factors (hereinafter abbreviated as "SPF") were calculated in accordance with the following equation so as to determine the skin-protecting effects of the individual compounds. As controls, the cream base of Example 3 (Comparative Product No. 1) and petrolatum (Comparative Product No. 2) were used.

$$SPF = \frac{\text{Minimum UV-A irradiation time period required to develop erythema on the skin coated with a product of this invention}}{\text{Minimum UV-A irradiation time period required to develop erythema on the uncoated skin}}$$

From the results of the present Test, it is understood that the application of the cream base or petrolatum was not able to protect the skin from ultraviolet radiation but the creams containing 2% of the compounds of this invention all showed SPF values around 6–8 and were all able to protect the skins effectively from UV-A ray.

EXAMPLE 2

[o/w-Type Cream]

An o/w-type cream was prepared by mixing the below-described components in a usual manner.
[Composition]

| | |
|---|---|
| 4-Methoxy-2'-carboxydibenzoylmethane | 2.0 wt. % |
| Stearic acid | 1.0 |
| Hydrophobic monostearic glyceride | 2.0 |
| Polyoxyethylenesorbitan monostearate | 1.0 |
| Cetyl alcohol | 1.0 |
| Stearyl alcohol | 1.0 |
| Squalane | 10.0 |
| Liquid paraffin | 20.0 |
| Petrolatum | 5.0 |
| Butyl paraben | 0.1 |
| Methyl paraben | 0.1 |
| Triethanolamine | 1.0 |
| Glycerin | 10.0 |
| Perfume | suitable amount |
| Water | balance |
| | 100.0 |

EXAMPLE 3

[w/o-Type Cream]

A w/o-type cream was prepared by mixing the below-described components in a usual manner.
[Composition]

| | |
|---|---|
| 4-Methoxy-2'-carboxydibenzoylmethane | 2.0 wt. % |
| Sorbitan sesquioleate | 4.0 |
| Aluminum stearate | 0.5 |
| Cetyl alcohol | 4.0 |
| Liquid paraffin | 16.0 |
| Squalane | 10.0 |
| Isopropyl myristate | 5.0 |

-continued

| | |
|---|---|
| Sodium benzoate | 0.3 |
| Glycerin | 10.0 |
| Perfume | suitable amount |
| Water | balance |
| | 100.0 |

EXAMPLE 4

[o/w-Type Milky Lotion]

An o/w-type milky lotion was prepared by mixing the below-described components in a usual manner.
[Composition]

| | |
|---|---|
| 4-Methoxy-2'-carboxydibenzoylmethane sodium salt | 3.0 wt. % |
| Stearic acid | 2.0 |
| Sorbitan monostearate | 1.5 |
| Polyoxyethylenesorbitan monostearate | 1.0 |
| Cetyl alcohol | 0.4 |
| Stearyl alcohol | 0.3 |
| Isopropyl myristate | 7.0 |
| Squalane | 5.0 |
| Liquid paraffin | 5.0 |
| Solid paraffin | 2.0 |
| Ethyl paraben | 0.1 |
| Methyl paraben | 0.1 |
| Carbopol | 0.2 |
| Caustic soda | 0.4 |
| Perfume | suitable amount |
| Water | balance |
| | 100.0 |

EXAMPLE 5

[Skin Lotion]

A skin lotion was prepared by mixing the below-described components in a usual manner.
[Composition]

| | |
|---|---|
| 4-Methoxy-2'-carboxydibenzoylmethane arginine salt | 2.0 wt. % |
| Polyoxyethylene(23)lauryl ether | 4.0 |
| Ethanol | 10.0 |
| Glycerin | 3.0 |
| Dipropylene glycol | 7.0 |
| Lactic acid | 0.05 |
| Sodium lactate | 0.12 |
| Methyl paraben | 0.1 |
| Perfume | suitable amount |
| Colorant | small amount |
| Water | balance |
| | 100.0 |

What is claimed is:

1. 4-Methoxy-2'-carboxydibenzoylmethane of the following formula (I):

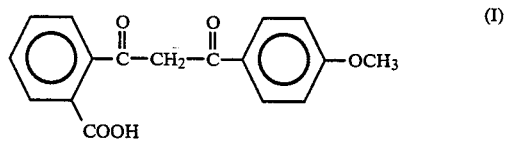

or a salt thereof, said salt comprising a lithium, a sodium, a potassium, a lysine, an arginine, a monoethanolamine, a diethanolamine, or a triethanolamine salt.

2. The 4-methoxy-2'-carboxydibenzoylmethane of claim 1.

3. A salt of the 4-methoxy-2'-carboxydibenzoylmethane of claim 1.

4. A sodium salt of the 4-methoxy-2'-carboxydibenzoylmethane of claim 1.

5. An arginine salt of the 4-methoxy-2'-carboxydibenzoylmethane of claim 1.

6. A composition comprising 4-methoxy-2'-carboxydibenzoylmethane or a salt thereof in association with a cosmetically acceptable diluent or carrier.

7. The composition of claim 6, where the composition is an o/w-type cream.

8. The composition of claim 6, where the composition is an o/w-type milky lotion.

9. The composition of claim 6, where the composition is an skin lotion.

10. The composition of claim 6, comprising 4-methoxy-2'-carboxydibenzoylmethane, stearic acid, a hydrophobic monostearate glyceride, a polyoxyethylenesorbitan monostearate, cetyl alcohol, stearyl alcohol, squalane, liquid paraffin, petrolatum, butyl paraben, methyl paraben, triethanolamine, glycerin, perfume and water.

11. The composition of claim 6, comprising 4-methoxy-2'-carboxydibenzoylmethane, sorbitan sesquioleate, aluminum stearate, cetyl alcohol, liquid paraffin, squalane, isopropyl myristate, sodium benzoate, glycerin, perfume and water.

12. The composition of claim 6, comprising 4-methoxy-2'-carboxydibenzoylmethane sodium salt, stearic acid, sorbitan monostearate, a polyoxyethylenesorbitan monostearate, cetyl alcohol, stearyl alcohol, isopropyl myristate, squalane, liquid paraffin, solid paraffin, ethyl paraben, methyl paraben, carbopol, caustic soda, perfume, and water.

13. The composition of claim 6, comprising 4-methoxy-2'-carboxydibenzoylmethane arginine salt, a polyoxyethylene(23)lauryl ether, ethanol, glycerin, dipropylene glycol, lactic acid, sodium lactate, methyl paraben, perfume, a colorant, and water.

14. A method for protecting skin from ultraviolet radiation, comprising applying to the said skin an effective amount of 4-methoxy-2'-carboxydibenzoylmethane or a salt thereof.

15. The method of claim 14, comprising applying to the said skin a sodium salt or an arginine salt of 4-methoxy-2'-carboxydibenzoylmethane.

* * * * *